United States Patent

Masaki et al.

[11] Patent Number: 5,523,317
[45] Date of Patent: Jun. 4, 1996

[54] METHOD OF REDUCING BLOOD PRESSURE

[75] Inventors: Mitsuo Masaki, Chiba; Fumiyo Hara, Kanagawa; Toshiro Kamishiro, Saitama, all of Japan

[73] Assignee: Nippon Chemiphar Co., Ltd., Tokyo, Japan

[21] Appl. No.: 188,446

[22] Filed: Jan. 26, 1994

Related U.S. Application Data

[63] Continuation-in-part of Ser. No. 95,093, Jul. 20, 1993, abandoned.

[30] Foreign Application Priority Data

Jul. 5, 1993 [JP] Japan .................................. 5-191689
Dec. 1, 1993 [JP] Japan .................................. 5-329818

[51] Int. Cl.$^6$ .................................................. A01N 43/50
[52] U.S. Cl. ............................................................ 514/398
[58] Field of Search ............................................... 514/398

[56] References Cited

PUBLICATIONS

CA 120:69232 1993.

*Primary Examiner*—Paul J. Killos
*Attorney, Agent, or Firm*—McAulay Fisher Nissen Goldberg & Kiel

[57] ABSTRACT

Disclosed is a method of reducing blood pressure which comprises administering to a patient an imidazole derivative of the formula:

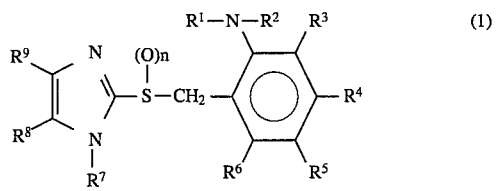

wherein:
each of $R^1$ and $R^2$ is hydrogen, substituted or unsubstituted alkyl, alkoxyalkyl, cycloalkyl, aryl, aralkyl, or $R^1$ and $R^2$ are combined to form hetero ring; each of $R^3$, $R^4$, $R^5$ and $R^6$ is hydrogen, halogen, substituted or unsubstituted alkoxy, substituted or unsubstituted alkyl, aryl, aryloxy, alkoxycarbonyl, nitro, amino, acyl, or $R^3$ is combined with $R^2$ to form heteroring; $R^7$ is hydrogen, substituted or unsubstituted alkyl, substituted or unsubstituted aryl, substituted or unsubstituted arylcarbonyl, or S-containing heteroring; each of $R^8$ and $R^9$ is hydrogen, halogen, substituted or unsubstituted alkoxy, unsubstituted or substituted alkyl, alkoxycarbonyl, aralkyl, nitro, amino, acyl, substituted or unsubstituted aryl, or $R^8$ and $R^9$ are combined to from alkylene; and n is 0 or 1.

6 Claims, No Drawings

1

METHOD OF REDUCING BLOOD PRESSURE

This application is a continuation-in-part of Ser. No. 08/095,093, filed on Jul. 20, 1993, now abandoned, the contents of which are hereby incorporated by reference.

BACKGROUND OF THE INVENTION

1. Field of Invention

The present invention relates to a method of reducing blood pressure using an antihypertensive agent (or hypotensive agent) of a new type.

2. Description of Prior Art

As antihypertensive agents, there have been known various compounds belonging to various groups. Representative antihypertensive agents are as follows:

Ganglion blocking agents such as Hexamethonium bromide and Trimetaphan camsilate;

Hydralazine agents such as Todralazine hydrochloride, Hydralazine hydrochloride, Cadralazine, and Budralazine;

Rauwolfiae Radix agents such as Alseroxylon, Dimethylaminoethyl reserpilinate dihydrochloride, Syrosingopine, Rauwolfia alkaloids, Rescinnamine, and Reserpine;

Sympatholytic agents such as Guanethidine sulfate, and Bethanidine sulphate;

$\alpha_2$ Agonists such as Guanfacine hydrochloride, Clonidine hydrochloride, Guanabenz acetate, and Methyldopa;

Alkaloids such as Dihydroergotoxine mesilate;

$\alpha_1$ Blockers such as Urapidil, Terazosinn hydrochloride, Bunazosin hydrochloride, Prazosin hydrochloride, and Doxazosin mesilate;

β-Blockers such as Carteolol hydrochloride, Bunitrolol hydrochloride, Propranolol hydrochloride, Methoprolol tartarate, Nipradilol, Pindolol, and Penbutolol sulfate;

α,β-Blockers such as Amosulalol hydrochloride and Labetalol hydrochloride;

Ca-Antagonists such as Nicardipine hydrochloride, Manidipine hydrochloride, Nisoldipine, Nitrendipine, and Nilvadipine;

ACE Inhibitors such as Alacepril, Delapril hydrochloride, Captopril, Cilazapril, Enalapril maleate, and Lisinopril;

Diuretics such as Indapamide, Tripamide, Furosemide, and Meticrane.

SUMMARY OF THE INVENTION

An object of the present invention is to provide a new antihypertensive agent (or hypotensive agent) of a type differing from those of known types such as described above.

The present invention resides in a method of reducing blood pressure which comprises adiministering to a patient an imidazole derivative having the formula (1):

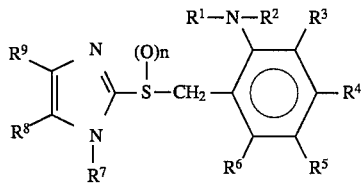

Wherein:

each of $R^1$ and $R^2$ independently is hydrogen atom, an alkyl group having 1–8 carbon atoms, an alkyl group of 2–6 carbon atoms having an alkoxy group of 1–4 carbon atoms, a cycloalkyl group having 5–8 carbon atoms, an aryl group having 6–12 carbon atoms, an aralkyl group having 1–4 carbon atoms in its alkyl moiety and 6–12 carbon atoms in its aryl moiety, an aralkyl group having 1–4 carbon atoms in its alkyl moiety and 6–12 carbon atoms in its aryl moiety which has at least one substituent selected from the group consisting of an alkoxy group of 1–4 carbon atoms and a halogen atom, or an alkyl group of 1–8 carbon atoms having 1–3 halogen atoms, or $R^1$ and $R^2$ are combined to form, together with nitrogen atom to which $R^1$ and $R^2$ are attached, one of 5–8 membered heterocyclic rings;

each of $R^3$, $R^4$, $R^5$ and $R^6$ independently is hydrogen atoms, a halogen atom, an alkoxy group having 1–6 carbon atoms, an alkyl group having 1–6 carbon atoms, an aralkyl group having 1–4 carbon atoms in its alkyl moiety and 6–12 carbon atoms in its aryl moiety, an aralkyloxy group having 1–4 carbon atoms in its alkyl moiety and 6–12 carbon atoms in its aryl moiety, an alkoxycarbonyl group having 2–7 carbon atoms, nitro group, amino group, an acyl having 1–7 carbon atoms, an alkyl group of 1–6 carbon atoms which has 1–3 halogen atoms, or an alkoxy group of 1–6 carbon atoms which has 1–3 halogen atoms, or $R^3$ is combined with $R^2$ to form, together with nitrogen atom to which $R^2$ is attached and two carbon atoms of benzene ring to which $R^3$ is attached, one of 5–8 membered heterocyclic rings;

$R^7$ is a hydrogen atom, an alkyl group having 1–6 carbon atoms, an alkyl group of 1–6 carbon atoms which has at least one substituent selected from the group consisting of an aryl group of 4–12 carbon atoms, hydroxyl group and a halogen atom, an aryl group having 4–12 carbon atoms, an aryl group of 4–12 carbon atoms which has at least one substituent selected from the group consisting of an alkyl group of 1–6 carbon atoms, an alkoxy group of 1–6 carbon atoms, and a halogen atom, an arylcarbonyl group having 7–13 carbon atoms, an arylcarbonyl group of 7–13 carbon atoms which has at least one substituent selected from the group consisting of an alkyl group of 1–6 carbon atoms, an alkoxy group of 1–6 carbon atoms, and a halogen atom, or a 5–8 membered heterocyclic group containing a sulfur atom as its ring member;

each of $R^8$ and $R^9$ independently is a hydrogen atom, a halogen atom, an alkoxy group having 1–6 carbon atoms, an alkyl group having 1–6 carbon atoms, an alkoxycarbonyl group having 2–7 carbon atoms, an aralkyl group having 1–4 carbon atoms in its alkyl moiety and 6–12 carbon atoms in its aryl moiety, nitro group, amino group, an acyl group having 1–7 carbon atoms, an alkyl group of 1–6 carbon atoms having 1–3 halogen atoms, an alkoxy group of 1–6 carbon atoms having 1–3 halogen atoms, an aryl group having 6–12 carbon atoms, or an aryl group of 6–12 carbon atoms, which has at least one substitutent selected from the group consisting of an alkyl group of 1–6 carbon atoms, an alkoxy group of 1–6 carbon atoms and a halogen atom, or $R^8$ and $R^9$ are combined to form an alkylene chain of 3–5 carbon atoms; and n is 0 or 1.

The present invention is based on the new finding made by the present inventors that the imidazole derivatives of the above formula(1) show prominent effect for reducing blood pressure of mammals.

DETAILED DESCRIPTION OF THE INVENTION

The imidazole derivatives of the formula (1) per se are known and can be prepared in the manner described in Chem. Pharm. Bull., 39(7), pp. 1746 (1991), Chem. Pharm. Bull., 40(3), pp. 675–682 (1992), Japanese Patent Priovisional Publications No. 2(1990)-128263, No.3(1991)-163065, No.1(1989)-131175, and No.64(1989)-63575. It is known that these imidazole derivatives show excellent anti-ulcer actions.

Details of the groups and atoms mentioned for the formula (1) are described below.

$R^1$ and $R^2$ are the same or different from each other and each represents hydrogen atom; an alkyl group having 1–8 carbon atoms such as methyl, ethyl, propyl, isopropyl, butyl, isobutyl, pentyl, isopentyl, neopentyl, hexyl, heptyl, octyl or 2-ethylhexyl; an alkyl group of 2–6 carbon atoms having an alkoxy group of 1–4 carbon atoms such as methoxyethyl, methoxypropyl, methoxybutyl, methoxypentyl, ethoxyethyl, ethoxypropyl, ethoxybutyl, propoxyethyl, propoxypropyl or butoxyethyl; a cycloalkyl group having 5–8 carbon atoms such as cyclopentyl, cyclohexyl, cycloheptyl, or cyclooctyl; an aryl group having 6–12 carbon atoms such as phenyl, naphthyl, tolyl, or xylyl; an aralkyl group which has 6–12 carbon atoms in its aryl moiety and 1–4 carbon atoms in its alkyl moiety such as benzyl, phenylethyl, naphthylmethyl, tolylmethyl or xylylmethyl; an aralkyl group having 1–4 carbon atoms in its alkyl moiety and 6–12 carbon atoms in its aryl moiety which has at least one substituent selected from the group consisting of an alkoxy group of 1–4 carbon atoms and a halogen atom, such as methoxybenzyl, trimethoxybenzyl, trimethoxyphenylethyl or chlorophenylethyl, an alkyl group of 1–8 carbon atoms having 1 to 3 halogen atoms such as chloromethyl, chloroethyl, bromomethyl, fluoromethyl, fluoroethyl, fluoropropyl, fluorobutyl, difluoromethyl, trifluoromethyl, of trifluoroethyl. Otherwise, $R^1$ and $R^2$ are combined to from, in conjunction with the nitrogen atom to which $R^1$ and $R^2$ are attached, one of 5–8 membered heterocyclic rings such as pyrrole ring, pyrroline ring, pyrrolidine ring, pyridine ring, piperidine ring, or perhydroazepine ring.

$R^3$, $R^4$, $R^5$ and $R^6$ are, all or in part, the same or different from each other, and each represents hydrogen atoms; a halogen atom such as fluorine, chlorine, or bromine; an alkoxy group having 1–6 carbon atoms such as methoxy, ethoxy, propoxy, isoproxy, butoxy, isobutoxy, tert-butoxy, pentoxy or hexyloxy; an alkyl group having 1–6 carbon atoms such as methyl, ethyl, propyl, isopropyl, butyl, isobutyl, tert-butyl, pentyl or hexyl; an aralkyl group which has 6–12 carbon atoms in its aryl moiety and 1–4 carbon atoms in its alkyl moiety such as benzyl, phenylethyl, naphthylmethyl tolylmethy or xylylmethyl; an aralkyloxy group which has 6–12 carbon atoms in its aryl moiety and 1–4 carbon atoms in its alkoxy moiety such as benzyloxy, phenylethyloxy, naphthylmethyloxy or tolylmethyloxy; an alkoxycarbonyl having 2–7 carbon atoms such as methoxycarbonyl, ethoxycarbonyl, propoxycarbonyl, isopropoxycarbonyl; butoxycarbonyl, pentoxycarbonyl or hexyloxycarbonyl; nitro group; amino group; an acyl having 1–7 carbon atoms such as formyl, acetyl, propionyl, isopropionyl, butyryl, isobutyryl, valeryl, or isovaleryl; an alkyl group of 1–6 carbon atoms which has 1 to 3 halogen atoms such as fluoromethyl, chloromethyl, bromomethyl, difluoromethyl, trifluoromethyl, fluoroethyl, trifluoroethyl, fluoropropyl, fluorobutyl, fluoropentyl, or fluorohexyl; or an alkoxy group of 1–6 carbon atoms which has 1 to 3 halogen atoms such as fluoromethoxy; chloromethoxy, bromomethoxy, difluoromethoxy, trifluoromethoxy, fluoroethoxy, fluoropropoxy, fluoroisopropoxy, fluorobutoxy, fluoropentoxy, or fluorohexyloxy. Otherwise, $R^3$ is combined with $R^2$ to form, together with the nitrogen atom to which $R^2$ is attached and two carbon atoms of benzene ring to which $R^3$ is attached, one of 5- to 8-membered rings. Examples of the fused ring of the 5- to 8-membered ring with the benzene ring include 1,2,3,4-tetrahydroquinoline, 2,3,4,5-tetrahydrobenz[b]azepine and indoline.

$R^7$ is a hydrogen atom; an alkyl group of 1–6 carbon atoms which may be substituted with one or more aryl groups of 4–12 carbon atoms, hydroxyl groups, or halogen atoms such as methyl, ethyl, propyl, isopropyl, butyl, isobutyl, t-butyl, pentyl, benzyl, phenylethyl, phenylpropyl, tolylmethyl, xylylmethyl, naphthylmethyl, naphthylethyl, hydroxymethyl, hydroxyethyl, hydroxypropyl, hydroxybutyl, fluoromethyl, 2-(2-pyridyl)ethyl, fluoroethyl, fluoropropyl, trifluoromethyl, chloromethyl, or bromomethyl; an aryl group of 4–12 carbon atoms which may be substituted with an alkyl group of 1–6 carbon atoms, an alkoxy group of 1–6 carbon atoms, or a halogen atom, such as phenyl, naphthyl, tolyl, xylyl, methoxyphenyl, ethoxyphenyl, dimethoxyphenyl, chlorophenyl, fluorophenyl, bromophenyl, 3-pyridyl, 2-pyridyl, 3-methyl-2-pyridyl, or 5-trifluoromethyl-2-pyridyl; an arylcarbonyl of 7–13 carbon atoms which may be substituted with an alkyl group of 1–6 carbon atoms, an alkoxy group of 1–6 carbon atoms, or a halogen atom, such as benzoyl, tolylcarbonyl, methoxybenzoyl, ethoxybenzoyl, or fluorobenzoyl; or a heterocyclic group of 5–8 members having a sulfur atom as its ring member, such as thienyl or tetrahydrothienyl.

$R^8$ and $R^9$ are the same or different from each other, and each represents hydrogen atom; a halogen atom such as fluorine, chlorine, bromine or iodine; an alkoxy group having 1–6 carbon atoms such as methoxy, ethoxy, propoxy, butoxy, isobutoxy, pentoxy, or hexyloxy; an alkyl group having 1–6 carbon atoms such as methyl, ethyl, propyl, isopropyl, butyl, isobutyl, pentyl or hexyl; an alkoxycarbonyl group having 2–7 carbon atoms, such as methoxycarbonyl, ethoxycarbonyl, propoxycarbonyl, butoxycarbonyl, isobutoxycarbonyl, pentoxycarbonyl, or hexyloxycarbonyl; nitro group; amino group; an acyl group having 1–7 carbon atoms such as formyl, acetyl, propionyl, butyryl, isobutyryl, valeryl or isovaleryl; an alkyl group of 1–6 carbon atoms having 1 to 3 halogen atoms, such as fluoromethyl, chloromethyl, bromomethyl, difluoromethyl, trifluoromethyl, flouroetyl, trifluoroethyl, fluoropropyl, flouorobutyl, fluoropentyl or fluorohexyl; an alkoxy group of 1–6 carbon atoms having 1 to 3 halogen atoms, such as flouromethoxy, chloromethoxy, bromomethoxy, difluoromethoxy, trifluoromethoxy, fluoroethoxy, fluoropropoxy, flouorobutoxy, fluoropentoxy or fluorohexyloxy; or an aryl group (e.g., phenyl and naphthyl) which may have at least one substitutent (generally one, two or three substituents) selected from the group consisting of an alkyl group of 1–6 carbon atoms (e.g., methyl, ethyl, propyl, isopropyl, butyl or isobutyl), an alkoxy group of 1–6 carbon atoms (e.g., methoxy, ethoxy, propoxy, isopropoxy, butoxy, or isobutoxy) and a halogen atom (e.g., fluorine, chlorine, or bromine), such as phenyl, naphthyl, tolyl, xylyl, methoxyphenyl, ethoxyphenyl, dimethoxyphenyl, chlorophenyl, fluorophenyl, or bromophenyl. Otherwise, $R^8$ and $R^9$ are combined to from an alkylene chain of 3–6 carbon atoms. In other words, $R^8$ and $R^9$ are combined to form, together with two carbon atoms of the imidazole ring to which $R^8$ and $R^9$ are attached, one of 5–7 membered alicyclic rings such as cyclopentenyl, cyclohexenyl, methylcyclohexenyl, dimethylcyclohexenyl or cycloheptenyl.

"n" for number of oxygen atoms is 0 or 1.

The following groups are preferably adopted for the imidazole derivative of the formula (1).

1) Each of $R^1$ and $R^2$ independently is hydrogen atom, an alkyl group of 1–8 carbon atoms, an alkyl group of 2–6 carbon atoms having an alkoxy group of 1–4 carbon atoms or aralkyl group having 1–4 carbon atoms in its alkyl moiety and 6–12 carbon atoms in its aryl moiety substituted with alkoxy group of 1–4 carbon atoms.

2) Each of $R^3$, $R^4$ and $R^6$ is hydrogen atom, and $R^5$ is hydrogen atom, an alkoxy group of 1–6 carbon atoms or halogen atom.

3) $R^7$ is hydrogen atom.

4) each or $R^8$ and $R^9$ of the formula is a hydrogen atom.

5) "n" is 1.

Representative examples of the imidazole derivatives represented by the formula (1) are those which have $R^1$, $R^2$, $R^3$, $R^4$, $R^5$, $R^6$, $R^7$, $R^8$ and $R^9$ as defined in Table 1.

TABLE 1

| No | $R^1$ | $R^2$ | $R^3$ | $R^4$ | $R^5$ | $R^6$ | $R^7$ | $R^8$ | $R^9$ |
|---|---|---|---|---|---|---|---|---|---|
| 1 | H | H | H | H | H | H | Ph | H | H |
| 2 | H | Me | H | H | H | H | Ph | H | H |
| 3 | Me | Me | H | H | H | H | Ph | H | H |
| 4 | Et | Et | H | H | H | H | Ph | H | H |
| 5 | Me | Me | H | H | H | H | (p-MeO)Ph | H | H |
| 6 | Me | Me | H | H | H | H | (p-Cl)Ph | H | H |
| 7 | H | H | H | H | H | H | H | H | H |
| 8 | H | Me | H | H | H | H | H | H | H |
| 9 | Me | Me | H | H | H | H | H | H | H |
| 10 | H | Me | H | H | H | H | Me | H | H |
| 11 | H | Me | H | H | H | H | t-Bu | H | H |
| 12 | H | Me | H | H | H | H | COPh | H | H |
| 13 | H | Me | H | H | H | H | 3-thienyl | H | H |
| 14 | H | Me | H | H | H | H | H | Cl | H |
| 15 | H | Me | H | H | H | H | H | n-Bu | H |
| 16 | H | Me | H | H | H | H | H | $CO_2Et$ | H |
| 17 | H | Me | H | H | H | H | H | Ph | H |
| 18 | H | Me | H | H | H | H | H | $NO_2$ | H |
| 19 | H | Me | Me | H | H | H | H | H | H |
| 20 | H | Me | H | H | Me | H | H | H | H |
| 21 | H | Me | H | H | H | Me | H | H | H |
| 22 | H | Me | H | Me | H | Me | H | H | H |
| 23 | H | Me | H | Me | OMe | Me | H | H | H |
| 24 | H | Me | H | H | OMe | H | H | H | H |
| 25 | H | Me | H | OMe | OMe | H | H | H | H |
| 26 | H | Me | H | H | OMe | OMe | H | H | H |
| 27 | H | Me | H | H | $OCF_3$ | H | H | H | H |
| 28 | H | Me | H | $NO_2$ | H | H | H | H | H |
| 29 | H | Me | H | Cl | H | H | H | H | H |
| 30 | H | Me | H | H | H | H | $CH_2CH_2OH$ | H | H |
| 31 | H | Me | H | H | H | H | H | Me | H |
| 32 | H | Me | H | H | Me | H | H | Me | H |
| 33 | H | Me | H | H | OMe | H | H | Me | H |
| 34 | H | Et | H | H | H | H | H | Me | H |
| 35 | H | Et | H | H | Me | H | H | Me | H |
| 36 | H | Et | H | H | OMe | H | H | Me | H |
| 37 | H | i-Bu | H | H | H | H | H | Me | H |
| 38 | H | Me | H | H | H | H | H | Et | H |
| 39 | H | Me | H | H | H | H | H | $CF_3$ | H |
| 40 | H | Me | H | H | H | H | H | $CH_2CF_3$ | H |
| 41 | H | Me | H | H | OEt | H | H | H | H |
| 42 | H | Me | H | H | OBzl | H | H | H | H |
| 43 | H | Et | H | H | H | H | H | H | H |
| 44 | H | Et | H | H | Me | H | H | H | H |
| 45 | H | Et | H | H | OMe | H | H | H | H |
| 46 | H | Pr | H | H | H | H | H | H | H |
| 47 | H | i-Pr | H | H | H | H | H | H | H |
| 48 | H | i-Bu | H | H | H | H | H | H | H |
| 49 | H | i-Bu | H | H | Me | H | H | H | H |
| 50 | H | i-Bu | H | H | OMe | H | H | H | H |
| 51 | H | NeoPentyl | H | H | H | H | H | H | H |
| 52 | H | Hex | H | H | H | H | H | H | H |
| 53 | H | c-Pent | H | H | H | H | H | H | H |
| 54 | H | c-Hex | H | H | H | H | H | H | H |
| 55 | H | $CH_2CF_3$ | H | H | H | H | H | H | H |
| 56 | H | Ph | H | H | H | H | H | H | H |
| 57 | H | Bzl | H | H | H | H | H | H | H |
| 58 | H | Et | H | H | OMe | Me | H | H | H |
| 59 | H | i-Bu | H | H | OMe | Me | H | H | H |
| 60 | —$(CH_2)_4$— | | H | H | H | H | H | H | H |
| 61 | H | —$(CH_2)_3$— | | H | H | H | H | H | H |
| 62 | H | Me | H | H | H | H | i-Pr | H | t-Bu |
| 63 | H | Me | H | H | H | H | H | Me | Me |
| 64 | H | H | H | H | H | H | H | Et | Et |
| 65 | H | Me | H | H | H | H | H | Et | Et |

TABLE 1-continued

| No | R¹ | R² | R³ | R⁴ | R⁵ | R⁶ | R⁷ | R⁸ | R⁹ |
|---|---|---|---|---|---|---|---|---|---|
| 66 | H | Me | H | H | H | H | H | Me | Et |
| 67 | Me | Me | H | H | H | H | H | Et | Et |
| 68 | H | Me | H | H | H | H | H | Pr | Et |
| 69 | H | Me | H | H | H | H | H | Ph | Ph |
| 70 | H | i-Bu | H | H | H | H | H | Et | Et |
| 71 | H | H | H | H | Me | H | H | Et | Et |
| 72 | H | Et | H | H | H | H | H | Et | Et |
| 73 | H | H | H | H | H | H | H | —(CH₂)₄— | |
| 74 | H | Me | H | H | H | H | H | —(CH₂)₄— | |
| 75 | Me | Me | H | H | H | H | H | —(CH₂)₄— | |
| 76 | H | Et | H | H | H | H | H | —(CH₂)₄— | |
| 77 | H | i-Bu | H | H | H | H | H | —(CH₂)₄— | |
| 78 | H | Hex | H | H | H | H | H | —(CH₂)₄— | |
| 79 | H | H | H | H | Me | H | H | —(CH₂)₄— | |
| 80 | H | Me | H | H | Me | H | H | —(CH₂)₄— | |
| 81 | H | Me | H | H | H | Me | H | —(CH₂)₄— | |
| 82 | H | Me | H | Me | H | Me | H | —(CH₂)₄— | |
| 83 | H | Me | H | H | OMe | H | H | —(CH₂)₄— | |
| 84 | H | Me | H | H | OBzl | H | H | —(CH₂)₄— | |
| 85 | H | Me | H | Me | OMe | Me | H | —(CH₂)₄— | |
| 86 | H | Me | H | H | OCF₃ | H | H | —(CH₂)₄— | |
| 87 | H | Me | H | Cl | H | H | H | —(CH₂)₄— | |
| 88 | H | —(CH₂)₃— | | H | H | H | H | —(CH₂)₄— | |
| 89 | H | c-Hex | H | H | H | H | H | —(CH₂)₄— | |
| 90 | H | c-Pent | H | H | H | H | H | —(CH₂)₄— | |
| 91 | | —(CH₂)₅— | H | H | H | H | H | —(CH₂)₄— | |
| 92 | H | Me | H | H | H | H | H | —CH₂C(CH₂)₂—<br>\|<br>(Me)₂ | |
| 93 | H | Me | H | H | H | H | H | —(CH₂)₃C—<br>\|<br>(Me)₂ | |
| 94 | H | Me | H | H | H | H | H | —(CH₂)₃— | |
| 95 | H | Me | H | H | H | H | H | —(CH₂)₅— | |
| 96 | H | i-Bu | H | H | OMe | OMe | H | H | H |
| 97 | H | i-Bu | H | H | OCF₃ | H | H | H | H |
| 98 | H | i-Bu | H | H | Cl | H | H | H | H |
| 99 | H | i-Bu | H | H | NO₂ | H | H | H | H |
| 100 | H | i-Bu | H | H | H | OMe | H | H | H |
| 101 | H | i-Bu | H | H | F | H | H | H | H |
| 102 | H | i-Bu | H | H | H | Me | H | H | H |
| 103 | H | i-Bu | H | Cl | H | H | H | H | H |
| 104 | H | i-Bu | H | Me | H | H | H | H | H |
| 105 | H | i-Bu | H | H | H | Cl | H | H | H |
| 106 | H | i-Bu | Me | H | H | H | H | H | H |
| 107 | H | i-Bu | OMe | H | H | H | H | H | H |
| 108 | H | Bu | H | H | H | H | H | H | H |
| 109 | H | CH₂—Ph(4-OMe) | H | H | H | H | H | H | H |
| 110 | H | CH₂—Ph(3,4,5-(OMe)₃) | H | H | H | H | H | H | H |
| 111 | H | CH₂—Ph(2,4-Me₂) | H | H | H | H | H | H | H |
| 112 | H | CH₂CH₂—Ph(4-Cl) | H | H | OMe | H | H | H | H |
| 113 | H | Me | H | H | CO₂Me | H | H | H | H |
| 114 | H | Me | H | NH₂ | H | H | H | H | H |
| 115 | H | H | H | H | Ac | H | H | H | H |
| 116 | H | Me | H | i-Bu | H | H | H | H | H |
| 117 | H | Me | H | H | O-i-Pr | H | H | H | H |
| 118 | H | Me | H | H | i-Bu | H | H | H | H |
| 119 | H | t-Bu | H | H | H | H | H | H | H |
| 120 | H | i-Pen | H | H | H | H | H | H | H |
| 121 | H | CH₂CH₂OMe | H | H | H | H | H | H | H |
| 122 | H | CH₂CH₂OMe | H | H | Me | H | H | H | H |
| 123 | H | CH₂CH₂OMe | H | H | H | Me | H | H | H |
| 124 | Me | CH₂CH₂OMe | H | H | H | H | H | H | H |
| 125 | H | CH₂CH₂OEt | H | H | H | H | H | H | H |
| 126 | H | (CH₂)₃OMe | H | H | H | H | H | H | H |
| 127 | H | CH₂CH₂O-i-Pr | H | H | H | H | H | H | H |
| 128 | H | (CH₂)₃OEt | H | H | OMe | H | H | H | H |
| 129 | H | (CH₂)₄OMe | H | OCF₃ | H | H | H | H | H |
| 130 | H | CH₂CH₂Opr | H | OMe | OMe | H | H | H | H |
| 131 | Me | CH₂CH₂OBu | H | Cl | H | H | H | H | H |
| 132 | H | CH₂CH₂OEt | H | H | Me | H | H | H | H |
| 133 | H | CH₂CH₂OMe | H | Me | OMe | Me | H | H | H |
| 134 | H | CH₂CH₂OEt | H | Me | OMe | Me | H | H | H |
| 135 | H | CH₂CH₂OMe | H | Cl | OMe | H | H | H | H |
| 136 | H | CH₂CH₂OMe | H | CF₃ | OMe | H | H | H | H |

TABLE 1-continued

| No | R¹ | R² | R³ | R⁴ | R⁵ | R⁶ | R⁷ | R⁸ | R⁹ |
|---|---|---|---|---|---|---|---|---|---|
| 137 | H | CH₂CH₂OMe | H | H | OMe | H | H | H | H |
| 138 | Me | Me | H | H | H | H | MePy | H | H |
| 139 | Me | Me | H | H | H | H | 2-Py | H | H |
| 140 | H | i-Pen | H | H | Me | H | H | H | H |
| 141 | H | i-Bu | H | H | Et | H | H | H | H |
| 142 | H | Pen | H | H | Me | H | H | H | H |
| 143 | H | CH₂CH₂—Ph(3,4,5-(OMe)₃) | H | H | Me | H | H | H | H |
| 144 | H | CH₂CH₂OMe | H | H | OEt | H | H | H | H |
| 145 | Me | —(CH₂)₃— | | H | H | H | H | H | H |
| 146 | Me | i-Bu | H | H | OMe | H | H | H | H |
| 147 | Me | CH₂CH₂OMe | H | H | OMe | H | H | H | H |
| 148 | H | CH₂CH₂OMe | H | H | Et | H | H | H | H |
| 149 | H | CH₂CH₂OEt | H | H | Et | H | H | H | H |
| 150 | H | CH₂CH₂OEt | H | H | OMe | H | H | H | H |
| 151 | H | Me | H | H | Bzl | H | H | H | H |

Remarks:
H: hydrogen, Me: methyl, Et: ethyl, Pr: propyl, i-Pr: isopropyl, Bu: butyl, i-Bu: isobutyl, t-Bu: tert-butyl, i-Pen: isopentyl, Hex: hexyl, c-Hex: cyclohexyl, c-Pent: cyclopentyl, Ph: phenyl, Bzl: benzyl, CF₃: tri-fluoromethyl, OMe: methoxy, O-i-Pr: isopropoxy, OCF₃: trifluoromethoxy, Ac: acetyl, CO₂Et: ethoxycarbonyl, OBzl: benzyloxy, COPH: benzoyl, MePy: 3-methyl-2-pyridyl, 2-Py: 2-pyridyl.

Examples of the imidazole derivatives according to the formula (1) are listed below:

2-[[5-methoxy-(2-methoxyethyl)amino]benzylsulfinyl]imidazole
2-[[2-(2-methoxyethyl)amino]benzylsulfinyl]imidazole,
2-[[2-(2-isopropoxyethyl)amino]benzylsulfinyl]imidazole
2-[[2-(2-methoxyethyl)amino-5-methyl]benzylsulfinyl]imidazole
2-[[2-(2-methoxyethyl)amino-6-methyl]benzylsulfinyl]imidazole
2-[[2-(2-ethoxyethyl)amino]benzylsulfinyl]imidazole,
2-[[2-(2-ethoxypropyl)amino]benzylsulfinyl]imidazole,
2-[[2-(2-ethoxyethyl)amino-5-methyl]benzylsulfinyl]imidazole,
2-[[4,6-dimethyl-5-methoxy-2-(2-methoxyethyl)amino] benzylsufinyl]imidazole,
2-[(2-methylamino)benzylthio]-4,5,6,7-tetrahydro-1 H-benzimidazole,
2-[(2-methylamino)benzylsulfinyl]-4,5,6,7-tetrahydro-1 H-benzimidazole,
2-[(2-dimethylamino)benzylthio]-4,5,6,7-tetrahydro-1 H-benzimidazole,
2-[(2-dimethylamino)benzylsulfinyl]-4,5,6,7-tetrahydro-1 H-benzimidazole,
2-[(2-amino)benzylthio]-4,5,6,7-tetrahydro-1 H-benzimidazole
2-[(2-amino)benzylsulfinyl]-4,5,6,7-tetrahydro-1H-benzimidazole,
2-[(2-methylamino)benzylthio]imidazole,
2-[(2-methylamino)benzylsulfinyl]imidazole,
2-[(2-isobutylamino)benzylthio]imidazole,
2-[(2-isobutylamino)benzylsulfinyl]imidazole,
2-[(2-dimethylamino)benzylthio]imidazole,
2-[(2-dimethylamino)benzylsulfinyl]imidazole,
2-[(5-methyl-2-methylamino)benzylthio]imidazole,
2-[(5-methyl-2-methylamino)benzylsulfinyl]imidazole,
2-[(2-amino)benzylthio]imidazole,
2-[(2-amino)benzylsulfinyl]imidazole,
2-[(2-isobutylamino-5-nitro)benzylthio]imidazole,
2-[(2-isobutylamino-5-nitro)benzylsulfinyl]imidazole,
2-[(4-chloro-2-isobutylamino)benzylthio]imidazole,
2-[(4-chloro-2-isobutylamino)benzylsulfinyl]imidazole,
2-[(2-isopropylamino)benzylthio]imidazole,
2-[(2-isopropylamino)benzylsulfinyl]imidazole,
2-[(2-ethylamino)benzylthio]imidazole,
2-[(2-ethylamino)benzylsulfinyl]imidazole,
2-[(2-benzylamino)benzylthio]imidazole,
2-[(2-benzylamino)benzylsulfinyl]imidazole,
2-[(2-isobutylamino-5-methoxy)benzylthio]imidazole,
2-[(2-isobutylamino-5-methoxy)benzylsulfinyl]imidazole
2-[(2,3-dimethoxy-6-isobutylamino)benzylthio]imidazole
2-[(2,3-dimethoxy-6-isobutylamino)benzylsulfinyl]imidazole,
2-[(2-methyl-6-methylamino)benzylthio]imidazole,
2-[(2-methyl-6-methylamino)benzylsulfinyl]imidazole,
2-[(2-isobutylamino-5-trifluoromethoxy)benzylthio]imidazole
2-[(2-isobutylamino-5-trifluoromethoxy)benzylsulfinyl] imidazole,
4-methyl-2-[(2-methylamino)benzylthio]imidazole,
4-methyl-2-[(2-methylamino)benzylsulfinyl]imidazole,
2-[(5-chloro-2-isobutylamino)benzylthio]imidazole,
2-[(5-chloro-2-isobutylamino)benzylsulfinyl]imidazole,
2-[(2-isobutylamino-6-methoxy)benzylthio]imidazole,
2-[(2-isobutylamino-6-methoxy)benzylsulfinyl]imidazole
2-[(5-fluoro-2-isobutylamino)benzylthio]imidazole,
2-[(5-fluoro-2-isobutylamino)benzylsulfinyl]imidazole,
2-[(2-isobutylamino-6-methyl)benzylthio]imidazole,
2-[(2-isobutylamino-6-methyl)benzylsulfinyl]imidazole,
2-[(2-isobutylamino-4-methyl)benzylthio]imidazole,
2-[(2-isobutylamino-4-methyl)benzylsulfinyl]imidazole,
2-[(2-chloro-6-isobutylamino)benzylthio]imidazole,
2-[(2-chloro-6-isobutylamino)benzylsulfinyl]imidazole,
2-[(2-isobutylamino-3-methyl) benzylthio]imidazole,
2-[(2-isobutylamino-3-methyl)benzylsulfinyl]imidazole,
2-[(2-isobutylamino-3-methoxy)benzylthio]imidazole,
2-[(2-isobutylamino-3-methoxy)benzylsulfinyl]imidazole
2-[(3-methyl-2-methylamino)benzylthio]imidazole,
2-[(3-methyl-2-methylamino)benzylsulfinyl]imidazole,
2-[(2-propylamino)benzylsulfinyl]imidazole,
2-[(2-butylamino)benzylsulfinyl]imidazole,
2-[(2-isobutylamino)benzylthio]-4,5,6,7-tetrahydro-1 H-benzimidazole,
2-[(2-isobutylamino)benzylsulfinyl]-4,5,6,7-tetrahydro-1 H-benzimidazole,
4-ethyl-5-methyl-2-[(2-methylamino)benzylthio]imidazole
4-ethyl-5-methyl-2-[(2-methylamino)benzylsulfinyl]imidazole
2-[(2-dimethylamino)benzylsulfinyl]-1(3-methylpyridin-2-yl)imidazole, 2-[2-(2,2,2-trifluoroethylamino)benzylsulfinyl]imidazole,
2-[8-(1,2,3,4-tetrahydro)quinolyl]methylsulfinylimidazole,
2-[(2-dimethylamino)benzylsulfinyl]-1-(2-fluorophenyl)imidazole
2-[(2-dimethylamino)benzylsulfinyl]-1-(2-pyridyl)imidazole,
2-[(2-morpholino)benzylsulfinyl]-1-(2-pyridyl)imidazole,
2-[(2-cyclohexylamino)benzylsulfinyl]-1-(2-pyridyl)imidazole,
2-[(2-dimethylamino)benzylsulfinyl]-1-(5-methoxy-2-pyridyl)imidazole,
2-[(2-dimethylamino)benzylthio]-1-methylimidazole,
2-[(2-dimethylamino)benzylthio]-1-(3-fluorophenyl)imidazole,
2-[(2-dimethylamino)benzylthio]-1-phenylimidazole,
2-[(2-dimethylamino)benzylthio]-1-(2-trifluoromethylphenyl)imidazole,
2-[(2-isopentylamino-5-methyl)benzylsulfinyl]imidazole,
2-[(5-ethyl-2-isobutylamino)benzylsulfinyl]imidazole,
2-[(5-methyl-2-pentylamino)benzylsulfinyl]imidazolel,
2-[[5-methyl-2-[2-(3,4,5-trimethoxyphenyl)ethyl]amino]benzylsulfinyl]imidazole,
2-[[5-ethoxy-2-(2-methoxyethyl)amino]benzylsulfinyl]imidazole,
2-[(1-methyl-1,2,3,4-tetrahydroquinolin-8-yl)methylsulfinyl]imidazole,
2-[[2-(isobutylmethylamino)-5-methoxy]benzylsulfinyl]imidazole,
2-[[5-methoxy-2-(2-methoxyethyl)methylamino]benzylsulfinyl]imidazole,
2-[[5-ethyl-2-(2-methoxyethyl)amino]benzylsulfinyl]imidazole,
2-[[2-(2-ethoxyethyl)amino-5-ethyl]benzylsulfinyl]imidazole,
2-[[2-(2-ethoxyethyl)amino-5-methoxy]benzylsulfinyl]imidazole, The imidazole derivative of the formula (1) according to the present invention can be administered either orally or parenterally to patients for reducing their blood pressure. Preparation forms for oral administration may be, for example, tablets, capsules, powder, granules, syrup and the like. Preparation forms for parenteral administration may be injectable preparations and suppositorys. For these preparations, excipients disintegrants, binders, lubricants, pigments, diluents, and the like which are commonly employed in the art may be used. The excipients may include dextrose, lactose and the like. Starch, carboxymethylcellulose calcium and the like may be used as the disintegrants. Magnesium stearate, talc and the like may be used as the lubricants. The binders may be hydroxypropylcellulose, gelatin, polyvinylpyrrolidone, gelatin, polyvinylpyrrolidone and the like.

The dose may usually be about 1 mg/day to 50 mg/day in the case of an injectable preparation and about 10 mg/day to 600 mg/day in the case of oral administration, both for an adult. The dose may be either increased or decreased depending on the age, race, and other conditions of the patients.

Examples of the present invention are given below.

EXAMPLE 1

2-[[5-Methoxy-2-(2-methoxyethyl)amino]benzylsulfinyl]imidazole (Intraperitoneal administration)

Under halothane anestheia, left femoral arteries of male spontaneously hypertensive rats (17–18 weeks old) were cannulated for blood pressure measurement. The animals were placed into the Bollman-type cages immediately after discontinuing the halothane inhalation.

Systemic blood pressure was measured using a pressure tranducer (TP-101T, available from Nihon Kohden Co., Ltd.) via a carrier amplifier (AP-621G, available from Nihon Kohden Co., Ltd.). Heart rate was measured with a cardiotachometer (AT-601G, available from Nihon Kohden Co., Ltd.) triggered by the pulse wave of systolic blood pressure. Both recordings were made on the thermo-pen-writing recorder (WT-687G, available from Nihon Kohden Co., Ltd.) simultaneously.

The test compound was given at the time of steady state of blood pressure and heart rate values approximately 1 hr. after the removal of anesthesia to avoid the influence of halothane. The test compound was suspended in an aqueous 1% methylcellulose solution at a concentration of 1% and administered intraperitoneally via the previously cannulated polyethylene tube.

In the case of administration of 20 mg/kg, the blood pressures prior to the administration which were 225 mmHg–145 mmHg (systolic blood pressure—diastolic blood pressure) lowered to 213 mmHg–128 mmHg after 15 min., 189 mmHg–107 mmHg after 1 hr., 191 mmHg–104 mmHg after 2 hrs., 197 mmHg–126 mmHg after 4 hrs., and 200 mmHg–131 mmHg after 5 hrs. Thus, the blood pressure was lowered effectively, and the lowered blood pressure was satisfactorily kept.

In the case of administration of 40 mg/kg, the blood pressures prior to the administration which were 243 mmHg–157 mmHg (systolic blood pressure—diastolic blood pressure) lowered to 209 mmHg–131 mmHg after 15 min., 177 mmHg–105 mmHg after 1 hr., 160 mmHg–96 mmHg after 2 hrs., 183 mmHg–110 mmHg after 4 hrs., and 185 mmHg–113 mmHg after 5 hrs. Thus, the blood pressure was satisfactorily kept.

In both cases, there was observed essentially no change of heart rate.

(Oral adminitration)

The test compound was suspended in an amount of 2 wt. % in an aqueous 1% methylcellulose solution containing 10 wt. % of sodium hydrogencarbonate. The resulting aqueous suspension was administered orally into male spontaneously hypertensive rats (weight 280–400 g, 15–20 week old) in the same manner as in the above intraperitoneal administration for measuring the actions on blood pressure.

The systolic blood pressure, diastolic blood pressure, and heart rate measured 1 hr., 2 hrs., 3 hrs., 4 hrs., 5 hrs., and 6 hrs., after the administration of the test compound in the amount of 40 mg/kg are set forth in Table 3.

EXAMPLE 2

2-[(2-Isobutylamino]benzylsulfinyl]imidazole

The measurement of change of blood pressures was carried out in the manner by intraperitoneal administration as described in Example 1, using the above imidazole derivative as test compound.

In the case of administration of 40 mg/kg, the blood pressures prior to the administration which were 214 mmHg–148 mmHg (systolic blood pressure—diastolic blood pressure) lowered to 203 mmHg–137 mmHg after 15 min., 174 mmHg–114 mmHg after 1 hr., 163 mmHg–109 mmHg after 2 hrs., 179 mmHg–117 mmHg after 4 hrs., and 181 mmHg–122 mmHg after 5 hrs. Thus, the blood pressure was lowered effectively, and the lowered blood pressure was satisfactorily kept.

There was observed essentially no change of heart rate.

EXAMPLE 3

2-[[8-(1,2,3,4-Tetrahydro)quinolyl]methylsulfinyl]imidazole

The measurement of change of blood pressures was carried out in the manner by intraperitoneal administration as described in Example 1, using the above imidazole derivative as test compound.

In the case of administration of 40 mg/kg, the blood pressures prior to the administration which were 217 mmHg–138 mmHg (systolic blood pressure—diastolic blood pressure) lowered to 190 mmHg–100 mmHg after 15 min., 170 mmHg–86 mmHg after 1 hr., 177 mmHg–91 mmHg after 2 hrs., 176 mmHg–100 mmHg after 4 hrs., and 179 mmHg–110 mmHg after 5 hrs. Thus, the blood pressure was lowered effectively, and the lowered blood pressure was satisfactorily kept.

There was observed essentially no change of heart rate.

The tested 2-[[8-(1,2,3,4-tetrahydro)quinolyl]methylsulfinyl]imidazole was prepared by the following method:

1,2,3,4-tetrahydro-8-quinolinemethanol (3.52 g, 22 mmol) was dissolved in dichloromethane (35 ml) and a solution of thionyl chloride (2.4 ml) in dichloromethane (10 ml) was added dropwise to the solution with ice-cooling for 10 min., and the resultant mixture was stirred for 30 min. The mixture was concentrated and the residue was suspended in dichloromethane (20 ml) and added gradually into a solution of 2-mercaptoimidazole (5.0 g) in ethanol (50 ml). The resultant mixture was stirred for 30 min. at room temperature, and concentrated to give a residue, which was treated with dichloromethane and aqueous sodium carbonate (5%). The organic layer was separated and dried over anhydrous sodium sulfate. Arter the evaporation of dichloromethane, the residue was treated by silica gel chromatography (ethyl acetate) for purification. 2-[[8-(1,2,3,4-tetrahydro)quinolyl]methylthio]imidazole was obtained as a yellow crystalline powder (1.88 g) from diethyl ether.

The obtained thioimidazole (1.80 g, 7.3 mmol) was dissolved in a mixture of chloroform (18 ml) and methanol (2 ml) and to this was added, with ice-cooling, for 30 min. m-chloroperbenzoic acid (85%, 1.49 g). After the completion of the reaction, chloroform and aqueous sodium carbonate (5%) were added to the reaction mixture and the separated organic later was washed with aqueous sodium hydroxide solution (0.05N, 20 ml) and then extracted with 2N aqueous sodium hydroxide solution (20 ml), which was washed with chloroform. To the aqueous layer was added portionwise an aqueous ammonium chloride solution (1N, 60 ml) with stirring to give a crystalline precipitate, which was washed sufficiently with water and dried. Pale yellow crystalline powder; yield 1.15 g.

m.p. 142°–144° C. (decomp.)

IR($v^{KBr}$) cm$^{-1}$: 3390, 3000, 2900, 1600, 1510, 1480, 1450, 1430, 1410, 1300, 1280, 1100, 1000, 940, 880, 780, 740, 500. NMR (CDCl$_3$/CD$_3$OD=1/1) δ: 1.86 (2H, m), 2.75 (2H, t, J=6 Hz), 3.28 (2H, t, J=5 Hz), 4.26 (1H, d, J=13 Hz), 4.43 (1H, d, J=13 Hz), 6.3–7.0 (3H, m), 7.24 (2H, s).

EXAMPLE 4

2-[(2-Ethylamino)benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs., and 5 hrs. after the administration are set forth in Table 2, respectively.

EXAMPLE 5

2-[(2-Isobutylamino-5-methoxy)benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs. and 5 hrs. after the administration are set forth in Table 2, respectively.

EXAMPLE 6

2[(5-Chloro-2-isobutylamino)benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs. and 5 hrs. after administration are set forth in Table 2, respectively.

EXAMPLE 7

2-[[2-(2-Methoxyethyl)amino]benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs. and 5 hrs. after the administration are set forth in Table 2, respectively.

EXAMPLE 8

2-[(2-Isopentylamino-5-methyl)benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs., and 5 hrs. after the administration are set forth in Table 2, respectively.

The above imidazole derivative was prepared in a manner similar to that described in Chem. Pharm. Bull., 40(3), pp.675–682 (1992).

m.p. 144°–146° C. (decomp.) IR($v^{KBr}$) cm$^{-1}$: 3370, 2950, 2910, 2860, 1620, 1580, 1520, 1465, 1440, 1310, 1100, 1035, 900, 805, 770, 500. NMR (CDCl$_3$/CD$_3$OD=1/1) δ: 0.96 (6H, d, J=6 Hz), 1.3–1.9 (3H, m), 2.15 (3H, s), 3.05 (2H, t, J=7 Hz), 4.28 (1H, d, J=14 Hz), 4.49 (1H, d, J=14 Hz), 6.4–7.1 (3H, m), 7.23 (2H, s).

EXAMPLE 9

2-[(5-Ethyl-2-isobutylamino]benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blook pressure and heart rate prior to, and at 15 min., 1 hr., 2 hrs., 4 hrs. and 5 hrs. after the administration are set forth in Table 2, respectively.

The above imidazole derivative was prepared in a manner similar to that deseribed in Chem. Pharm. Bull., 40(3), pp. 675–682 (1992).

m.p. 140°–142° C. (decomp.) IR($v^{KBr}$) cm$^{-1}$: 3390, 3340, 3100, 2950, 2920, 2870, 1620, 1580, 1520, 1465, 1420, 1310, 1100, 1025, 1010, 890, 810, 500. NMR (CDCl$_3$/CD$_3$OD=1/1) δ: 1.02 (6H, d, J=6 Hz), 1.10 (3H, t, J=7 Hz), 1.93 (1H, m), 2.44 (2H, q, J=7 Hz), 2.88 (2H, d, J=7 Hz), 4.29 (1H, d, J=13 Hz), 4.55 (1H, d, J=13 Hz), 6.4–7.1 (3H, m), 7.23 (2H, s).

EXAMPLE 10

2-[(5-Methyl-2-pentylamino)benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs. and 5 hrs. after the administration are set forth in Table 2, respectively.

The above imidazole derivative was prepared in a manner similar to that described in Chem. Pharm. Bull., 40 (3), pp. 675–682 (1992).

m.p. 138°–140° C. (decomp.) IR($v^{KBr}$) cm$^{-1}$: 3370, 2920, 2850, 2820, 1620, 1580, 1520, 1440, 1320, 1310, 1100, 1040, 960, 900, 800, 780, 500. NMR (CDCl$_3$/CD$_3$OD=1/1) δ: 0.80–1.9 (9H, m), 2.14 (3H, s), 3.03 (2H, t, J=7 Hz), 4.29 (1H, d, J=13 Hz), 4.50 (1H, d, J=13 Hz), 6.4–7.1 (3H, m), 7.24 (2H, s).

EXAMPLE 11

2-[[5-Methyl-2-[2-(3,4,5-trimethoxyphenyl)ethyl]amino]benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs., and 5 hrs. after the administration are set forth in Table 2, respectively.

The above imidazole derivative was prepared in a manner similar to that described in Chem. Pharm. Bull., 40(3), pp. 675–682(1992).

m.p. 125°–128° C. (decomp.) IR($v^{KBr}$) cm$^{-1}$: 3370, 3000, 2930, 2830, 1620, 1590, 1505, 1460, 1420, 1330, 1315, 1240, 1125, 1000. NMR (CDCl$_3$/CD$_3$OD=1/1) δ: 2.15 (3H, s), 2.88 (2H, t, J=7 Hz), 3.34 (2H, t, J=7 Hz), 3.79 (3H, s), 3.85 (6H, s), 4.24 (1H, d, J=14 Hz), 4.45 (1H, d, J=14 Hz), 6.4–7.1 (5H, m), 7.24 (2H, s).

EXAMPLE 12

2-[[2-(2-Ethoxyethyl)amino-5-methoxy]benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs., and 5 hrs. after administration are set forth in Table 2, respectively.

The measurement of change of blood pressures by oral administration was carried out in the same manner as in Example 1, using the above imidazole derivative as test compound.

In the case of administration of 40 mg/kg, systolic blood pressure, diastolic blood pressure and heart rate prior to, and at 1 hr., 2 hrs., 3 hrs., 4 hrs., 5 hrs., and 6 hrs. after the administration are set forth in Table 3, respectively.

The above imidazole derivative was prepared in a manner similar to that described in Chem. Pharm. Bull., 40(3), pp. 675–682 (1992).

m.p. 120°–5–122° C. (decomp.) IR($v^{KBr}$) cm$^{-1}$: 3350, 2960, 2850, 2750, 1515, 1440, 1420, 1290, 1230, 1205, 1110, 1030, 960, 800, 765, 495. NMR (CDCl$_3$/CD$_3$OD=1/1) δ: 1.22 (3H, t, J=7 Hz), 3.19 (2H, m), 3.5–3.8 (4H, m), 3.61 (3H, s), 4.22 (1H, d, J=14 Hz), 4.57 (1H, d, J=14 Hz), 6.34 (1H, d, J=3 Hz), 6.62 (1H, d, J=9 Hz), 6.75 (1H, dd, J=3, 9 Hz), 7.16 (2H, s), 11.32 (1H, bs).

EXAMPLE 13

2-[[5-Ethoxy-2-(2-methoxyethyl)amino]benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs. and 5 hrs. after the administration are set forth in Table 2, respectively.

The measurement of change of blood pressures by oral administration was carried out in the same manner as in Example 1, using the above imidazole derivative as test compound.

In the case of administration of 40 mg/kg, systolic blood pressure, diastolic blood pressure and heart rate prior to, and at 1 hr., 2 hrs., 3 hrs., 4 hrs., 5 hrs., and 6 hrs. after the administration are set forth in Table 3, respectively.

The above imidazole derivative was prepared in a manner similar to that described in Chem. Pharm. Bull., 40(3), pp. 675–682 (1992).

m.p. 118°–119° C. (decomp.) IR($v^{KBr}$) cm$^{-1}$: 3375, 2875, 2800, 1520, 1460, 1440, 1390, 1290, 1210, 1120, 1100, 1030, 960, 880, 490. NMR (CDCl$_3$) δ: 1.30 (3H, t, J=7 Hz), 3.19 (2H, t, J=5 Hz), 3.37 (3H, s), 3.5–3.7 (2H, m), 3.7–3.9 (2H, m), 4.24 (1H, d, J=14 Hz), 4.55 (1H, d, J=14 Hz), 6.3–6.8 (3H, m), 7.17 (2H, s).

EXAMPLE 14

2-[(1-Methyl-1,2,3,4-tetrahydroquinolin-8-yl)methylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs., and 5 hrs. after the administration are set forth in Table 2, respectively.

The measurement of change of blood pressures by oral administration was carried out in the same manner as in Example 1, using the above imidazole derivative as test compound.

In the case of administration of 40 mg/kg, ststolic blood pressure, diastolic blood pressure and heart rate prior to, and at 1 hr., 2 hrs., 3 hrs., 4 hrs., 5 hrs., and 6 hrs. after the administration are set forth in Table 3, respectively.

The above imidazole derivative was prepared in a manner similar to that described in Chem. Pharm. Bull., 40(3), pp. 675–682 (1992).

m.p. 130° C. (decomp.) IR($v^{KBr}$) cm$^{-1}$: 3400, 3030, 2975, 2905, 1440, 1405, 1390, 1310, 1260, 1230, 1160, 1140, 1080, 1060, 1035, 955, 940, 870, 830, 750, 500. NMR (CDCl$_3$) δ: 1.8–1.9 (2H, m), 2.76 (3H, s), 2.7–2.8 (2H, m), 2.9–3.0 (2H, m), 4.37 (1H, d, J=13 Hz), 4.68 (1H, d, J=13 Hz), 6.9–7.2 (5H, m).

EXAMPLE 15

2-[[2-(Isobutylmethylamino)-5-methoxy]benzylsulfinyl]imidazole

The measurement of change of blood pressures by intraperitoneal administration was carried out in the same manner as in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs., and 5 hrs. after the administration are set forth in Table 2, respectively.

The above imidazole derivative was prepared in a manner similar to that described in Chem. Pharm. Bull., 40(3), pp. 675–682 (1992).

m.p. 107° C. (decomp.) IR($v^{KBr}$)cm$^{-1}$: 3100, 2950, 1600, 1490, 1040, 960, 780. NMR (CDCl$_3$) δ: 0.92 (6H, d, J=6 Hz), 1.77 (1H, m), 2.5–2.6 (5H, m), 3.66 (3H, s), 4.42 (1H, d, J=12 Hz), 4.82 (1H, d, J=12 Hz), 6.5–7.2 (3H, m), 7.1–7.3 (2H, br).

EXAMPLE 16

2-[[5-Methoxy-2-(2-methoxyethyl)methylamino]benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs. and 5 hrs. after the administration are set forth in Table 2, respectively.

The above imidazole derivative was prepared in a manner similar to that described in Chem. Pharm. Bull., 40(3 ), pp. 675–682 (1992).

m.p. 67°–68 ° C. ( decomp.) IR($v^{KBr}$)cm$^{-1}$: 2880, 2830, 1490, 1430, 1240, 1210, 1100, 1050, 960, 830, 790, 500. NMR (CDCl$_3$) δ: 2.66 (3H, s), 3.03 (2H, m), 3.33 (3H, s), 3.47 (2H, t, J=5 Hz), 3.66 (3H, s), 4.50 (1H, d, J=12 Hz), 4.84 (1H, d, J=12 Hz), 6.6–7.2 (5H, m), 12.0–12.2 (1H, br).

EXAMPLE 17

2-[[5-Ethyl-2-(2-methoxyethyl)amino]benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs. and 5 hrs. after the administration are set forth in Table 2, respectively.

The measurement of change of blood pressures by oral administration was carried out in the manner as described in Example 1, using the above imidazole derivative as test compound.

In the case of administration of 40 mg/kg, systolic blood pressure, diastolic blood pressure and heart rate prior to, and at 1 hr., 2 hrs., 3 hrs., 4 hrs., 5 hrs., and 6 hrs. after the administration are set forth in Table 3, respectively.

The above imidazole derivative was prepared in a manner similar to that described in Chem. Pharm. Bull., 40(3), pp. 675–682 (1992).

m.p. 134°–135° C. (decomp.) IR($v^{KBr}$) cm$^{-1}$: 3370, 2950, 2890, 2870, 2800, 1610 1580, 1515, 1410, 1305, 1120, 1110 1090, 1000, 885. NMR (CDCl$_3$) δ: 1.07 (3H, t, J=7 Hz), 2.40 (2H, q, J=7 Hz), 3.1–3.3 (2H, m), 3.38 (3H, s), 3.5–3.7 (2H, m), 4.21 (1H, d, J=14 Hz), 4.55 (1H, d, J=14 Hz), 5.07 (1H, br), 6.5–7.0 (3H, m), 7.0–7.3 (2H,br).

EXAMPLE 18

2-[[2-(2-Ethoxyethyl)amino-5-ethyl]benzylsulfinyl]imidazole

The measurement of change of blood pressures by intraperitoneal administration was carried out in the manner as described in Example 1, using the above imidazole derivative as test compound.

In the case of administration of 40 mg/kg, systolic blood pressure, diastolic blood pressure and heart rate prior to, and at 15 min., 1 hr., 2 hrs., 4 hrs., and 5 hrs. after the administration are set forth in Table 2, respectively.

The above imidazole derivative was prepared in a manner similar to that described in Chem. Pharm. Bull., 40(3), pp. 675–682 (1992).

m.p. 115.5°–116° C. (decomp.) IR($v^{KBr}$) cm$^{-1}$: 3380, 2960, 2850, 1620, 1520, 1420, 1310, 1110, 1020, 1000, 890, 780, 500. NMR (CDCl$_3$) δ: 1.07 (3H, t, J=7HZ), 1.20 (3H, t, J=7 Hz), 2.40 (2H, q, J=7HZ), 3.1–3.3 (2H, m), 3.5–3.7 (4H, m), 4.22 (1H, d, J=14 Hz), 4.55 (1H, d, J=14 Hz), 5.02 (1H, br), 6.5–7.0 (3H, m), 7.0–7.3 (2H, br), 11.4 (1H, br).

TABLE 2

| Ex. | Parameter[1] | Prior to Administration | After Administration | | | | |
|---|---|---|---|---|---|---|---|
| | | | 15 min | 1 hr | 2 hrs | 4 hrs | 5 hrs |
| 4 | SBP(mmHg) | 239 | 218 | 206 | 217 | 220 | 218 |
| | DBP(mmHg) | 139 | 112 | 108 | 111 | 126 | 123 |
| | HR(bpm) | 370 | 450 | 448 | 455 | 456 | 455 |
| 5 | SBP(mmHg) | 237 | 237 | 222 | 220 | 225 | 214 |
| | DBP(mmHg) | 139 | 139 | 123 | 120 | 119 | 114 |
| | HR(bpm) | 460 | 453 | 448 | 434 | 444 | 439 |
| 6 | SBP(mmHg) | 236 | 250 | 230 | 230 | 220 | 229 |
| | DBP(mmHg) | 143 | 157 | 142 | 137 | 132 | 130 |
| | HR(bpm) | 370 | 380 | 370 | 380 | 410 | 410 |
| 7 | SBP(mmHg) | 253 | 234 | 210 | 213 | 219 | 226 |
| | DBP(mmHg) | 148 | 126 | 109 | 112 | 119 | 128 |
| | HR(bpm) | 450 | 446 | 405 | 401 | 430 | 440 |
| 8 | SBP(mmHg) | 238 | 249 | 231 | 210 | 205 | 202 |
| | DBP(mmHg) | 150 | 163 | 145 | 133 | 128 | 126 |
| | HR(bpm) | 420 | 410 | 419 | 411 | 385 | 380 |
| 9 | SBP(mmHg) | 246 | 248 | 230 | 217 | 206 | 205 |
| | DBP(mmHg) | 165 | 163 | 155 | 150 | 136 | 129 |
| | HR(bpm) | 395 | 360 | 360 | 380 | 366 | 371 |
| 10 | SBP(mmHg) | 248 | 227 | 217 | 209 | 202 | 200 |
| | DBP(mmHg) | 165 | 153 | 146 | 137 | 130 | 124 |
| | HR(bpm) | 430 | 360 | 414 | 400 | 386 | 380 |
| 11 | SBP(mmHg) | 217 | 208 | 202 | 190 | 189 | 195 |
| | DBP(mmHg) | 136 | 126 | 119 | 111 | 110 | 110 |
| | HR(bpm) | 440 | 445 | 426 | 429 | 430 | 440 |
| 12 | SBP(mmHg) | 242 | 208 | 168 | 179 | 207 | 214 |
| | DBP(mmHg) | 138 | 102 | 80 | 92 | 105 | 114 |
| | HR(bpm) | 475 | 483 | 433 | 435 | 475 | 475 |
| 13 | SBP(mmHg) | 260 | 225 | 190 | 200 | 228 | 225 |
| | DBP(mmHg) | 151 | 123 | 95 | 107 | 132 | 131 |
| | HR(bpm) | 458 | 460 | 411 | 403 | 450 | 477 |
| 14 | SBP(mmHg) | 248 | 160 | 168 | 201 | 205 | 207 |
| | DBP(mmHg) | 138 | 68 | 74 | 103 | 108 | 110 |
| | HR(bpm) | 470 | 450 | 375 | 377 | 405 | 400 |
| 15 | SBP(mmHg) | 268 | 249 | 228 | 230 | 229 | 219 |
| | DBP(mmHg) | 154 | 136 | 120 | 120 | 123 | 123 |
| | HR(bpm) | 450 | 450 | 443 | 442 | 440 | 430 |
| 16 | SBP(mmHg) | 251 | 250 | 232 | 223 | 227 | 226 |
| | DBP(mmHg) | 131 | 123 | 110 | 110 | 117 | 120 |
| | HR(bpm) | 460 | 478 | 472 | 461 | 450 | 445 |
| 17 | SBP(mmHg) | 227 | 193 | 160 | 165 | 152 | 133 |
| | DBP(mmHg) | 136 | 105 | 83 | 83 | 75 | 65 |
| | HR(bpm) | 452 | 480 | 420 | 401 | 383 | 350 |
| 18 | SBP(mmHg) | 248 | 210 | 215 | 219 | 208 | 200 |
| | DBP(mmHg) | 148 | 103 | 111 | 113 | 110 | 100 |
| | HR(bpm) | 525 | 528 | 489 | 480 | 492 | 475 |

[1]SBP: Systolic Blood Presure DBP: Diastolic Blood Presure. HR: Heart Rate.

TABLE 3

| Ex. | Parameter[1] | Prior to Administration | After Administration | | | | | |
|---|---|---|---|---|---|---|---|---|
| | | | 1 hr | 2 hrs | 3 hrs | 4 hrs | 5 hrs | 6 hrs |
| 1 | SBP(mmHg) | 242 | 210 | 199 | 210 | 202 | 222 | 213 |
| | DBP(mmHg) | 150 | 120 | 118 | 123 | 122 | 125 | 130 |
| | HR(bpm) | 452 | 428 | 430 | 429 | 440 | 460 | 455 |
| 12 | SBP(mmHg) | 245 | 218 | 213 | 205 | 196 | 197 | 210 |
| | DBP(mmHg) | 143 | 124 | 122 | 119 | 110 | 112 | 120 |
| | HR(bpm) | 490 | 477 | 460 | 445 | 424 | 418 | 440 |
| 13 | SBP(mmHg) | 239 | 216 | 208 | 203 | 199 | 197 | 200 |
| | DBP(mmHg) | 144 | 125 | 115 | 118 | 113 | 118 | 118 |
| | HR(bpm) | 475 | 464 | 456 | 439 | 426 | 421 | 420 |
| 14 | SBP(mmHg) | 270 | 247 | 244 | 239 | 237 | 236 | 226 |
| | DBP(mmHg) | 156 | 134 | 135 | 132 | 133 | 132 | 130 |
| | HR(bpm) | 477 | 385 | 379 | 372 | 364 | 345 | 338 |
| 17 | SBP(mmHg) | 240 | 200 | 181 | 185 | 182 | 180 | 184 |
| | DBP(mmHg) | 145 | 109 | 93 | 100 | 98 | 97 | 103 |
| | HR(bpm) | 475 | 464 | 456 | 439 | 426 | 421 | 420 |

[1]SBP: Systolic Blood Pressure
DBP: Diastolic Blood Pressure
HR: Heart Rate

EXAMPLE 19

Preparation Example (Tablets)

Each tablet (220 mg) contained the following components

| Imidazole derivative | 50 mg |
|---|---|
| Lactose | 103 |
| Starch | 50 |
| Magnesium stearate | 2 |
| Hydroxypropylcellulose | 15 |

EXAMPLE 20

Preparation Example (Capsules)

Each hard gelatin capsule (350 mg) contained the following components:

| Imidazole derivative | 40 mg |
|---|---|
| Lactose | 200 |
| Starch | 70 |
| Polyvinylpyrrolidone | 5 |
| Crystalline cellulose | 35 |

EXAMPLE 21

Preparation Example (Granules)

Each granule (1 g) contained the following components:

| Imidazole derivative | 200 mg |
|---|---|
| Lactose | 450 |
| Corn starch | 300 |
| Hydroxypropylcellulose | 50 |

What is claimed is:

1. A method of reducing blood pressure which comprises administering to a patient an imidazole derivative having the formula

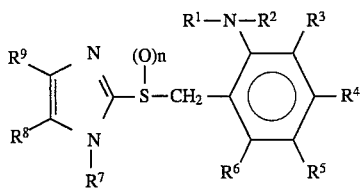

(1)

wherein:

each of $R^1$ and $R^2$ independently is hydrogen atom, an alkyl group having 1–8 carbon atoms, an alkyl group of 2–6 carbon atoms having an alkoxy group of 1–4 carbon atoms, a cycloalkyl group having 5–8 carbon atoms, an aryl group having 6–12 carbon atoms, an aralkyl group having 1–4 carbon atoms in its alkyl moiety and 6–12 carbon atoms in its aryl moiety, 4-methoxybenzyl, 3,4,5-trimethoxybenzyl, 2,4-dimethylbenzyl, 4-chlorophenethyl, or an alkyl group of 1–8 carbon atoms having 1–3 halogen toms, or $R^1$ and $R^2$ are combined to form, together with nitrogen atom to which $R^1$ and $R^2$ are attached, one of 5–8 membered heterocyclic rings;

each of $R^3$, $R^4$, $R^5$ and $R^6$ independently is hydrogen atoms, a halogen atom, an alkoxy group having 1–6 carbon atoms, an alkyl group having 1–6 carbon atoms, an aralkyl group having 1–4 carbon atoms, in its alkyl moiety and 6–12 carbon atoms, in its aryl moiety, an aralkyloxy group having 1–4 carbon atoms in its alkoxy moiety and 6–12 carbon atoms in its aryl moiety, an alkoxycarbonyl group having 2–7 carbon atoms, nitro group, amino group, an acyl having 1–7 carbon atoms, an alkyl group of 1–6 carbon atoms having 1–3 halogen atoms, or an alkoxy group of 1–6 carbon atoms having 1–3 halogen atoms, or $R^3$ is combined with $R^2$ to form, together with nitrogen atom to which $R^2$ is attached and two carbon atoms of benzene ring to which $R^3$ is attached, one of 5–8 membered heterocyclic rings;

$R^7$ is a hydrogen atom, an alkyl group having 1–6 carbon atoms, an alkyl group of 1–6 carbon atoms which has at least one substituent selected from the group consisting of an aryl group of 4–12 carbon atoms and a halogen atom, an aryl group having 4–12 carbon atoms, an aryl group of 4–12 carbon atoms which has at least one substituent selected from the group consisting of an alkyl group of 1–6 carbon atoms, an alkoxy group of 1–6 carbon atoms, and a halogen atom, an arylcarbonyl group having 7–13 carbon atoms, an arylcarbonyl group of 7–13 carbon atoms which has at least one substituent selected from the group consisting of an alkyl group of 1–6 carbon atoms, an alkoxy group of 1–6 carbon atoms, and a halogen atom, or a 5–8 membered heterocyclic group containing a sulfur atom as its ring member;

each of $R^8$ and $R^9$ independently is a hydrogen atom, a halogen atom, an alkoxy group having 1–6 carbon atoms, an alkyl group having 1–6 carbon atoms, an alkoxycarbonyl group having 2–7 carbon atoms, an aralkyl group having 1–4 carbon atoms in its alkyl moiety and 6–12 carbon atoms in its aryl moiety, nitro group, amino group, an acyl group having 1–7 carbon atoms, an alkyl group of 1–6 carbon atoms having 1–3 halogen atoms, an alkoxy group of 1–6 carbon atoms having 1–3 halogen atoms, an aryl group having 6–12 carbon atoms, or an aryl group of 6–12 carbon atoms which has at least one substituent selected from the group consisting of an alkyl group of 1–6 carbon atoms, an alkoxy group of 1–6 carbon atoms and a halogen atom, or $R^8$ and $R^9$ are combined to form an alkylene chain of 3–5 carbon atoms; and n is 0 or 1.

2. The method of reducing blood pressure as defined in claim 1, wherein each of $R^8$ and $R^9$ of the formula is hydrogen atom.

3. The method of reducing blood pressure as defined in claim 1, wherein each of $R^1$ and $R^2$ of the formula independently is hydrogen atom, an alkyl group of 1–8 carbon atoms, an alkyl group of 2–6 carbon atoms having an alkoxy group of 1–4 carbon atoms or aralkyl group having 1–4 carbon atoms in its alkyl moiety and 6–12 carbon atoms in its aryl moiety substituted with alkoxy group of 1–4 carbon atoms.

4. The method of reducing blood pressure as defined in claim 1, wherein each of $R^3$, $R^4$ and $R^6$ of the formula is hydrogen atom, and $R^5$ is hydrogen atom, an alkyl group of 1–6 carbon atoms or halogen atoms.

5. The method of reducing blood pressure as defined in claim 1, wherein $R^7$ of the formula is hydrogen atom.

6. The method of reducing blood pressure as defined in claim 1, wherein n of the formula is 1.

* * * * *